United States Patent [19]

Senaratne et al.

[11] Patent Number: 5,391,312
[45] Date of Patent: Feb. 21, 1995

[54] LUBRICANT ADDITIVES

[75] Inventors: K. Pushpananda A. Senaratne; Patrick S. Bynum; Mahmood Sabahi, all of Baton Rouge, La.

[73] Assignee: Albemarle Corportion, Richmond, Va.

[21] Appl. No.: 100,225

[22] Filed: Aug. 2, 1993

[51] Int. Cl.⁶ .................................... C10M 129/72
[52] U.S. Cl. ........................ 252/56 R; 252/52 R; 252/56 S; 252/72
[58] Field of Search ............ 252/56 R, 52 R, 72; C10M 129/26, 129/78; 106/33

[56] References Cited

FOREIGN PATENT DOCUMENTS 0218207 2/1986 European Pat. Off. .

Primary Examiner—Jacqueline V. Howard
Assistant Examiner—Cephia D. Toomer
Attorney, Agent, or Firm—Richard J. Hammond

[57] ABSTRACT

Seals contacted with lubricants, such as poly-α-olefin lubricants, are made to swell rather than shrink by the use of novel seal-swell agents which are effective even when used in amounts constituting less than 5% of the weight of the lubricant compositions. These seal-swell agents are ester oils composed of molecules corresponding to the formula $ROOC-CH_2CH_2-[(ROOC)CHCH_2]_m-C(COOR)_2-[CH_2CH(COOR)-]_n-CH_2CH_2COOR$ in which the R's represent alkyl groups of 1-30 carbons, and each of m and n represents zero or a positive integer such that the sum of m and n in a molecule is 0–30.

8 Claims, No Drawings

LUBRICANT ADDITIVES

FIELD OF THE INVENTION

This invention relates to lubricant additives and more particularly to novel seal-swell agents and to lubricant additive packages and lubricant compositions containing them.

BACKGROUND

As is known, the seals with which lubricants come into contact during use can be made from any of a variety of materials (generally an elastomer such as a nitrile rubber, an acrylic rubber, a silicone elastomer, or a fluoroelastomer) which can shrink in contact with some lubricants, such as poly-$\alpha$-olefins. Shrinkage of the seal, of course, can eventually result in leakage, so it is recognized to be desirable to incorporate seal-swell agents into lubricants in order to counteract the seal shrinkage that could be caused by the lubricant in the absence of the seal-swell agent.

The materials normally recommended for use as seal-swell agents are esters, which are ordinarily employed at concentrations of ~5%, based on the total weight of the lubricant composition. Of these esters, some are too volatile to be utilized in lubricant formulations that will be exposed to very high temperatures. Others, such as ditridecyl adipate, have practical utility and can provide adequate swelling of some seals when employed at the recommended 5% concentration. However, it would be desirable to find seal-swell agents that would be effective in swelling more seal materials and could be used in smaller concentrations since:

(1) the other additives commonly employed in lubricant compositions (e.g., viscosity improvers, pour point depressants, extreme pressure agents, antioxidants, and antiwear agents) have to be in balance to work effectively, (2) the inclusion of another additive, such as a seal-swell agent, upsets this balance, thus decreasing the effectiveness of each of these common additives, and (3) the degree to which the effectiveness of these additives is decreased by the inclusion of an additional additive, such as a seal-swell agent, appears to increase as the amount of the additional additive is increased.

SUMMARY OF INVENTION

The present invention resides in the use as seal-swell agents of ester oils composed of molecules corresponding to the formula ROOC—CH$_2$CH$_2$—[(ROOC)-CH—CH$_2$]$_m$—C(COOR)$_2$—[CH$_2$CH(COOR)-]$_n$—CH$_2$CH$_2$COOR in which the R's represent alkyl groups of 1-30 carbons, and each of m and n represents zero or a positive integer such that the sum of m and n in a molecule is 0-30. These seal-swell agents may be incorporated into lubricants by themselves or together with other additives as a part of a lubricant additive package.

DETAILED DESCRIPTION

The seal-swell agent ester oils used in the present invention are taught in application Ser. No. 07/947,629 (Sabahi et al.—I) and in Ser. No. 07/947,628 (Sabahi), both of which are abandoned, and to which application WO 93/13188, published on Jul. 8, 1993, claims priority, as well as in copending application Ser. No. 07/986,204 (Sabahi et al.—II). Those which are commercially available are sold by Ethyl Corporation as ETHYLUBE ® lubricants.

Essentially, these ester oils are compounds or mixtures which may be obtained by reacting suitable Michael donors and Michael acceptors and then, if desired, subjecting the products to post-treatments, such as transesterification. When produced directly by a Michael reaction, they are synthesized by reacting one or more dialkyl malonates with one or more alkyl acrylates. However, they may also be prepared by forming such a Michael product and then subjecting it to a transesterification reaction in which some of the alkyl groups are replaced with higher alkyl groups. The latter type of synthesis is particularly advantageous as a means of converting non-oily products of the Michael reaction to oils and/or permitting a variety of ester oils to be prepared from a particular Michael product via different transesterification reactions.

Although Michael donors and Michael acceptors which can be used in the reaction include all dialkyl malonates and alkyl acrylates in which the alkyl groups contain 1-30 carbons, the donors and acceptors which are sufficiently reactive to permit a reasonably fast reaction are apt to be preferred—even when their use leads to the formation of non-oily products that have to be transesterified to provide the desired oils. The alkyl groups in such compounds are preferably true alkyl groups (i.e., saturated aliphatic hydrocarbyl groups), such as methyl, ethyl, propyl, isopropyl, butyl, isobutyl, t-butyl, pentyl, hexyl, heptyl, octyl, decyl, dodecyl, tetradecyl, hexadecyl, octadecyl, eicosyl, docosyl, tetracosyl, and triacontyl groups, more preferably those containing 1-20 carbons, even more preferably those containing 1-10 carbons, and most preferably methyl and/or ethyl groups. However, they may also be groups which are predominantly alkyl in nature, i.e., contain one or more atoms other than the carbon and hydrogen of the alkyl groups as hetero atoms (e.g., oxygen, sulfur, or phosphorus atoms) which are part of the chain or as substituent groups (e.g., alkoxy, halo, or cyano groups) but contain so few of the other atoms that the predominantly hydrocarbyl nature of the groups is preserved.

To preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl groups to which they most closely correspond, so the term alkyl, as used herein, should be understood as including the predominantly alkyl groups as well as the alkyl groups normally denoted by those terms. Exemplary of such groups are chlorohexyl, bromodecyl, ethoxyoctyl, and cyanononyl.

As in Sabahi, it is generally preferred to prepare the Michael product by reacting the donor and acceptor in the presence of a basic initiator (preferably an alkali or alkaline earth metal hydroxide, alkoxide, amide, or carbonate) and a phase transfer catalyst (preferably an alkylammonium salt such as the tetraalkylammonium chlorides, bromides, fluorides, iodides, sulfates, hydrogen sulfates, carbonates, and phosphates in which the alkyl groups contain 1-20 carbons) at a suitable temperature, usually a temperature of about 0°-150° C., preferably about 20°-120° C., and most preferably about 60°-110° C.

The reaction is effected by combining the reactants, initiator, and catalyst, optionally in the presence of a solvent, and maintaining contact between the reactants at the selected reaction temperature until the desired degree of reaction has been effected. Since the reaction normally leads to the formation of a mixture of products containing different numbers of acceptor moieties per molecule, it permits the production of some molecules containing more acceptor moieties than the number that would theoretically be provided by the amount of acceptor employed in the reaction mixture. However, it is necessary for the reaction mixture to contain at least the stoichiometric requirement of the acceptor, and preferably a stoichiometric excess, in order for the product to contain a substantial amount of a desired product molecule. Thus, since the oils having optimum viscosities are usually those in which the molecules contain 1-30, preferably about 1-10 acceptor moieties/donor moiety, it is generally preferred for the acceptor/donor mol ratio in the reaction mixture to be about 1-35/1, more preferably about 1-15/1. Particularly preferred seal-swell agents of the invention are frequently ester oils which are prepared so as to have at least three acceptor molecules in at least about 25% of the molecules obtained by the Michael reaction.

The products of the Michael reaction may be liquids or solids, depending on the particular reactants and reactant ratios used; and, as already indicated, they are typically mixtures of compounds containing different numbers of acceptor moieties per molecule. If desired, the individual compounds of the mixture or groups of those compounds (e.g., the relatively low and relatively high molecular weight fractions) may be separated from one another prior to being used in their end application or prior to being subjected to transesterification preparatory to such use. However, such separations are frequently unnecessary and, in fact, sometimes undesirable. Having a product characterized by a wide molecular weight distribution can be an advantage in providing a balance of properties, such as a desired viscosity together with a desired solubility in the lubricant.

Achieving either a better balance of properties or properties which differ in some other respect from those of the Michael reaction product can also be accomplished by subjecting the product mixture or one or more of the components thereof to transesterification. Such a post-treatment of the Michael product is necessary when the Michael product is not an oil, and it is particularly beneficial in providing oily products containing ester groups which—if present in one or more of the Michael reactants—would make the reaction relatively slow. Thus, it is apt to be preferred, for example, to react dimethyl malonate with methyl acrylate to provide a first product and then transesterify that product with hexanol to provide an oily second product in which about a third of the functional groups are hexyl ester groups than to prepare an oily Michael reaction product from the slower-reacting dihexyl malonate and methyl acrylate.

Regardless of whether the transesterification is conducted on a recovered or unrecovered intermediate, it is accomplished by contacting the intermediate with one or more alcohols containing more carbons per molecule than the alkyl groups to be replaced and maintaining contact between the reactants at a suitable temperature until the desired transesterification has been effected. Alcohols most apt to be desirable for use in the reaction are substituted and unsubstituted alkanols containing up to about 30 carbons (e.g., ethanol, chloroethanol, propanol, butanol, hexanol, bromohexanol, heptanol, octanol, decanol, fluorodecanol, dodecanol, hexadecanol, octadecanol, eicosanol, tetracosanol, triacontanol, and mixtures thereof), as well as the aliphatic alcohols containing up to 30 carbons and also containing hetero atoms, such as oxygen, phosphorus, or sulfur (e.g., ethylthioethanol, ethoxyethanol, and the like).

The amount of alcohol employed in the transesterification reaction varies with the degree of transesterification desired, the quantity generally being the stoichiometric amount or an amount slightly in excess of the stoichiometric requirement. For example, when the intermediate contains an average of four ester groups per molecule, and the degree of transesterification desired is 75%, the amount of alcohol added to the intermediate should be three mols or slightly more than three mols/mol of intermediate. Only about two-thirds as much alcohol would be added, on the other hand, when the desired degree of transesterification is about 50%.

Use of a transesterification reaction after completion of the Michael reaction permits a wide variety of products to be prepared from any particular product of the Michael reaction. The transesterification is suitably conducted in the presence or absence of a basic catalyst at an elevated temperature which provides for reflux and removal of a lower alcohol by-product from the reaction mixture without permitting undue loss of the higher alcohol reactant(s) from the reaction vessel, e.g., a temperature of about 50°-180° C.

The products resulting from the Michael reaction or from conversion of the Michael reaction products to transesterified derivatives are typically washed with water to remove any unreacted materials and catalyst prior to being used in their intended application; and, if desired, they may then be further purified by subjecting them to fractional distillation.

Although any of the ester oils described above can be used as the instant seal-swell agents, those which are preferred are the ester oils that are composed of molecules corresponding to the formula $ROOC-CH_2CH_2-[(ROOC)CHCH_2]_m-C(COOR)_2-[CH_2CH(COOR)]_n-CH_2CH_2COOR$ in which the R's represent alkyl groups of 1-20, more preferably 1-10 carbons, and each of m and n represents zero or a positive integer such that the sum of m and n in a molecule is 0-10. It is frequently also preferred for the R's to represent two or three different alkyls, e.g., butyl and hexyl, or methyl, butyl, and hexyl.

When employed as seal-swell agents in the practice of the invention, these ester oils may be incorporated into any lubricant which can cause shrinkage of seals with which it comes into contact during use. However, they are most advantageously utilized as additives in the lubricants which are particularly apt to create this shrinkage problem with the seals that are usually preferred, i.e., seals made from elastomers such as nitrile rubbers, acrylic rubbers, silicone rubbers, and fluoroelastomers. Thus, in a preferred embodiment of the invention, the lubricants with which the novel seal-swell agents are used are the synthetic hydrocarbon lubricants, especially poly-α-olefin lubricants.

If desired, the seal-swell agents of the invention can be employed in concentrations as high as, or even higher than, those in which conventional seal-swell agents are used. However, since their advantage resides in their effectiveness at lower concentrations, they are normally used in amounts such that they constitute from about 0.5–5.0 percent, preferably from about 1–4 percent of the total weight of the lubricant composition.

The lubricant compositions of the invention desirably also contain one or more other additives of the types typically included in lubricant compositions, e.g., viscosity index improvers, lubricity additives, pour and/or floc point depressants, detergents, dispersants, extreme pressure agents, corrosion inhibitors, metal deactivators, antioxidants, thermal stabilizers, antifoaming agents, and antiwear agents. When such other additives are to be used, they are ordinarily the additives conventionally used to serve the aforementioned functions; and they may be incorporated into the lubricant before, after, and/or at the same time as the seal-swell agent. In the practice of the invention, it is frequently convenient to introduce the seal-swell agent as part of a lubricant additive package comprising a concentrate of all of desired additives in a portion of the lubricant. However, the effectiveness of the seal-swell agent is not diminished when all or some of the other desired additives are incorporated separately.

The invention is advantageous in its provision of lubricant compositions containing seal-swell agents which are effective in lower concentrations than are required for known seal-swell agents and which can be employed in high-temperature applications without volatilizing.

The following examples are given to illustrate the invention and are not intended as a limitation thereof. Unless otherwise specified, quantities mentioned in these examples are quantities by weight.

EXAMPLE 1

Reaction of Dimethyl Malonate with Methyl Acrylate

Charge a suitable reaction vessel with 792 g (6 mols) of dimethyl malonate, 52.8 g (0.4 mol) of potassium carbonate, 12 g (0.035 mol) of tetrabutylammonium hydrogen sulfate, and 1290 g (15 mols) of methyl acrylate. After stirring the reaction mixtures at room temperature for ~18 hours, slowly heat it to ~50° C. to effect a rapid rise of the temperature of the reaction mixture to reflux. Maintain the reaction mixture at reflux for ~15 minutes and then cool to room temperature over a period of ~1 hour. A heavy solid mass forms in the bottom of the reaction vessel during cooling. Dilute this mass with methylene chloride, wash with five 1.5-L portions of water, and subject the product to gas chromatographic (GC) analysis. The analysis shows the product to consist, in area percentages, of 4.3% trimethyl ester of 1,1,3-propanetricarboxylic acid, 70% tetramethyl ester of 1,3,3,5-pentanetetracarboxylic acid, 18% pentamethyl ester of 1,3,3,5,7-heptanepentacarboxylic acid, and 7.7% polyesters, i.e., products having more than five ester groups per molecule. Isolate the triester and tetraester components by fractional distillation under reduced pressure.

EXAMPLE 2

Reactions of Dimethyl Malonate with Methyl Acrylate

Conduct two additional Michael reactions between dimethyl malonate and methyl acrylate using tetrabutylammonium hydrogen sulfate as the phase transfer catalyst as in Example 1 but employing sodium methoxide as the base, 80° C. as the reaction temperature, and methyl acrylate/dimethyl malonate tool ratios of 8/1 (reaction mixture 2-A) and 10/1 (reaction mixture 1-B) respectively. Monitor the reactions be GC and discontinue them when the following analyses are obtained:

Reaction mixture 1-A: 32% tetramethyl ester of 1,3,3,5-pentanetetracarboxylic acid, 24% pentamethyl ester of 1,3,3,5,7-heptanepentacarboxylic acid, 11% hexamethyl ester of 1,3,5,5,7,9-nonanehexacarboxylic acid, 8% heptamethyl ester of 1,3,5,5,7,9,11-undecaneheptacarboxylic acid, 2% octamethyl ester of 1,3,5,7,7,9,11,13-tridecaneoctacarboxylic acid, and smaller amounts of higher esters.

Reaction mixture 2-B: 20% tetramethyl ester, 22% pentamethyl ester, 19% hexamethyl ester, 14% heptamethyl ester, 9% octamethyl ester, and smaller amounts of higher esters.

Then work up the product mixtures by diluting them with solvent, washing to neutrality with water, and removing solvent, water, and lower boiling products by distillation to form viscous oils which, in each case, are completely miscible with R-134a over a temperature range of −40° C. to 70° C.

EXAMPLE 3

Reaction of Dimethyl Malonate with Butyl Acrylate

Charge a suitable reaction vessel with 660 g (5 mols) of dimethyl malonate, 35 g (0.25 mol) of potassium carbonate, and 1.75g (0.005 mol) of tetrabutylammonium hydrogen sulfate. Heat the stirred mixture to 120° C., and add 2048 g (16 mols) of n-butyl acrylate over a period of six hours while monitoring the reaction by GC, which shows the dibutyl dimethyl ester of 1,3,3,5-pentanetetracarboxylic acid to be the major product at the end of this period. Then heat the reaction mixture at 150° C. for three hours to form a product mixture containing the tributyl dimethyl ester of 1,3,3,5,7-heptanepentacarboxylic acid. Cool the resulting reaction mixture to room temperature, add water and toluene, wash repeatedly with water until neutral, remove the water and toluene by azeotropic distillation, and then remove light products at 180°–185° C. and 0.1–0.15 mmHg to provide a heavy oil having a viscosity of 96 $mm^2.s^{-1}$ at 40° C., a viscosity of 11.6 $mm^2.s^{-1}$ at 100° C., a viscosity index of 109, and excellent miscibility with R-134a over a temperature range of −60° C. to 80° C.

EXAMPLE 4

Transesterification of Mixed Esters with Alcohol Mixture

Using a dimethyl malonate/methyl acrylate Michael reaction and workup procedure similar to that of the preceding examples, prepare a 20.8 g sample of a mixture of 66% tetramethyl ester of 1,3,3,5-pentanetetracarboxylic acid, 26% pentamethyl ester of 1,3,3,5,7-heptanepentaearboxylic acid, and 6% hexamethyl and heptamethyl esters. Treat the mixture with 0.1 mol of butanol and 0.1 mol of hexanol at 120° C. in the presence of a catalytic amount of 10% sodium methoxide, remove the volatiles by distillation and work up to provide an oil which has a viscosity of 159 $mm^2.s^{-1}$ at 40° C. viscosity of 14.6 $mm^2.s^{-1}$ at 100° C., a viscosity index of 88, and total miscibility with R134a.

EXAMPLE 5

Transesterification of Tetramethyl Ester with Alcohol Mixture

Charge a suitable reaction vessel with 660 g (2.2 mols) of the tetramethyl ester of Example 1, 406 g (4.4 mols) of n-butanol, 560 g (4.4 mols) of n-hexanol, and 5 mL of 5% sodium methoxide. Stir the reaction mixture magnetically and heat to ~110° C. to result in the slow distillation of methanol. After removing a stoichiometric amount of methanol, cool the reaction mixture to room temperature and dilute with toluene. After washing with water, remove the solvent and distill the crude oil under reduced pressure. The fraction collected at 195°–220° C. and 0.11–0.14 mm Hg is a water-white oil containing the tetraester product. This oil is miscible with R-134a refrigerant over a temperature of 40° C. to 70° C. and has a viscosity of 20–30 mm$^2$.s$^{-1}$ at 40° C., a viscosity index of 100, and a total acid number (TAN) of <0.05 mg KOH/gram.

EXAMPLE 6

Transesterification of 1,5-Dibutyl-3,3-dimethyl ester with 2-Ethylhexanol

Transesterify a crude reaction mixture of 85% 1,5-dibutyl-3,3-dimethyl ester of 1,3,3,5-pentanetetracarboxylic acid with 21 g (0.16 mol) of 1-ethyl-1-hexanol at 150°–200° C. under nitrogen. After removing the stoichiometric amount of methanol, cool the reaction mixture, dilute with toluene, wash to neutrality with water, and remove the water and toluene by azeotropic distillation. The resultant oil has a viscosity of 62.9 mm$^2$.s$^{-1}$ at 40° C., a viscosity of 7.9 mm$^2$.s$^{-1}$ at 100° C. a viscosity index of 88, and total miscibility with R-134a.

EXAMPLE 7

Transesterification of 3,3-Diethyl-1,5-dimethyl Ester with Butanol

Transesterify a 3,3-diethyl-1,5-dimethyl ester of 1,3,3,5-pentanetetracarboxylic acid with n-butanol in the presence of a catalytic amount of sodium methoxide by the general procedure of Example 5. The resulting product is totally miscible with R-134a refrigerant, has a viscosity of 19.2 mm$^2$.s$^{-1}$ at 40° C., a viscosity of 3.6 mm$^2$.s$^{-1}$ at 100° C., and a viscosity index of 40.

EXAMPLE 8

Transesterification of 3,3-Diethyl-1,5-dimethyl Ester with Alcohol Mixture

Repeat Example 7 except for replacing the butanol with a 1/1/1 mixture of n-hexanol, n-heptanol, and n-octanol. The resulting product is totally miscible with R-134a refrigerant at temperatures of 0°–70° C., has a viscosity of 22.3 mm$^2$.s$^{-1}$ at 40° C., a viscosity of 4.4 mm$^2$.s$^{-1}$ at 100° C., and a viscosity index of 107.

EXAMPLE 9

One-pot Michael Addition and Transesterification

Charge a reaction vessel with 15.8 Kg (120 mols) of dimethyl malonate, 158 g (1.2 mols) of potassium carbonate, and 37 g (0.1 mol) of tetrabutylammonium hydrogen sulfate under nitrogen. Heat the reactor to ~70° C., add 25.8 Kg (300 mols) of methyl acrylate over six hours, and then heat the reaction mixture at 70°–80° C. for at least 10 hours to form a product mixture containing a major amount of tetramethyl ester of 1,3,3,5-pentanetetracarboxylic acid, smaller amounts of pentamethyl and higher esters, and a minor amount of trimethyl ester of 1,1,3-propanetricarboxylic acid.

Charge 22 Kg (196 mols) of n-butanol and 30.3 Kg (206 mols) of n-hexanol to the reactor and heat at 110°–120° C. while collecting the volatiles overhead. After removing the stoichiometric amount of methanol, cool the reaction mixture to room temperature, dilute with toluene, wash to neutrality with water, dry by the azeotropic removal of water, and heat treat the crude under reduced pressure.

Distillation under reduced pressure (1 mmHg) and 200°–150° C. provides an oil which has a viscosity of 17 mm$^2$.s$^{-1}$ at 40° C., a viscosity of 3.6 mm$^2$.s$^{-1}$ at 100° C., a total acid number (TAN) at 0.025 mgKOH/g, a water content of 64 ppm, and total miscibility with R-134a over a temperature range of −60° C. to 80° C. The bottoms product is an oil having a viscosity of 24.8 mm$^2$.s$^{-1}$ at 40° C., a viscosity of 4.7 mm$^2$.s$^{-1}$ at 100° C., a total acid number of 0.034 mgKOH/g, a water content of 73 ppm, and total miscibility with R-134a over a temperature range of −60° C. to 80° C.

EXAMPLE 10

Reaction of Malononitrile with Acrylonitrile

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate under nitrogen. Slowly add 11.2 g (0.1 mol) of acrylonitrile at 50° C. with stirring and maintain the temperature at 50°–70° C. for 3 hours. Then cool the reaction mixture to room temperature, dissolve in ethyl acetate, wash with water until neutral, dry over magnesium sulfate, filter, and concentrate to provide a solid mass which spectroscopic analysis indicates to contain more than two acrylonitrile moieties per molecule.

EXAMPLE 11

Reaction of Malononitrile with Methyl Acrylate

Charge a reaction vessel with 3.3 g (0.05 mol) of malononitrile, 0.7 g (0.005 mol) of potassium carbonate, and 0.17 g (0.5 mmol) of tetrabutyl ammonium hydrogen sulfate. Heat the mixture to 50° C. under nitrogen and slowly add 10.8 g (0.125 mol) of methyl acrylate at a rate such as to maintain the temperature under 80° C. Keep the reaction mixture at 70°–80° C. for two hours, cool to room temperature, dilute with dichloromethane, wash with water until neutral, dry over magnesium sulfate, filter, and concentrate to provide a solid mass which spectroscopic analysis shows to contain dimethyl ester of 3,3-dicyano-1,5-pentanedicarboxylic acid, trimethyl ester of 5,5-dicyano-1,3,7-heptanetricarboxylic acid, and smaller amounts of higher molecular weight components.

EXAMPLE 12

Formulate four lubricant compositions by blending 12.5 parts of HiTEC® 953 additive (a commercial lubricant package sold by Ethyl Petroleum Additives, Inc. and composed primarily of a dispersant, overbased and neutral calcium sulfonates, an antiwear agent, and antioxidants), 11.0 parts of a commercial viscosity improver sold by Shell Oil Company as SHELLVIS® 251, and 0 or 5.0 parts of a seal-swell agent with 171.5 parts of a 5/1 mixture of poly-α-olefins having respective viscosities of 6 and 8 mm$^2$s$^{-1}$. The seal-swell agents employed in the compositions are shown below.

| Composition | Seal-Swell Agent |
|---|---|
| A | None |
| B | Ditridecyl adipate |
| C | Ketjenlube 135 - a commercial butanol ester of α-olefin-dicarboxylic acid copolymer sold by Akzo Chemicals and having a weight average molecular weight of 1800 |
| D | ETHYLUBE 25 - a malonate/acrylate oil having a viscosity of 25 $mm^2.s^{-1}$ and corresponding to the above ester oil formula in which the R's represent methyl, butyl, and hexyl groups and the sum of m and n in a molecule is an average of 0-2 |

EXAMPLE 13

Divide each of the lubricant compositions of Example 12 into three portions, and heat each of the portions in contact with a fluoroelastomer (FE), acrylic rubber (AR), or nitrile rubber (NR) seal material for 70 hours at 150° C. to test the effectiveness of the seal-swell agent. The seal materials employed in each of the compositions, as well as the results of the tests, are shown below.

| Lubricant | Volume Change (%) | | |
|---|---|---|---|
| Composition | In FE | In AR | In NR |
| A | −1.3 | −0.2 | −3.2 |
| B | 0.3 | 1.1 | −1.2 |
| C | 1.5 | −1.7 | −2.9 |
| D | 3.2 | 3.9 | 21.0 |

As demonstrated above, each of the seal materials shrinks in contact with the lubricant composition containing no seal-swell agent; and the known seal-swell agents are considerably less effective than the seal-swell agent of the invention in counteracting this shrinkage.

What is claimed is:

1. A composition comprising a lubricant and, as a seal-swell agent, an ester oil composed of molecules corresponding to the formula ROOC—$CH_2CH_2$—[(ROOC)CH—$CH_2$]$_m$—C(COOR)$_2$—[$CH_2$CH(COOR)]$_n$—$CH_2CH_2$COOR in which the R's represent alkyl groups of 1–30 carbons, and each of m and n represents zero or a positive integer such that the sum of m and n in a molecule is 0–30.

2. The composition of claim 1 wherein the lubricant is a synthetic hydrocarbon lubricant.

3. The composition of claim 2 wherein the synthetic hydrocarbon lubricant is a poly-α-olefin lubricant.

4. The composition of claim 1 wherein the ester oil is composed of molecules corresponding to the formula ROOC—$CH_2CH_2$—[(ROOC)CH$CH_2$]$_m$—C(COOR)$_2$—[$CH_2$CH(COOR)]$_n$—$CH_2CH_2$COOR in which the R's represent alkyl groups of 1–20 carbons, and each of m and n represents zero or a positive integer such that the sum of m and n in a molecule is 0–10.

5. The composition of claim 4 wherein the R's represent alkyl groups of 1–10 carbons.

6. The composition of claim 1 containing from about 0.05–5.0 percent by weight of the seal-swell agent.

7. The composition of claim 6 containing from about 1–4 percent by weight of the seal-swell agent.

8. The composition of claim 7 wherein the lubricant is a poly-α-olefin lubricant and the seal-swell agent is an ester oil composed of molecules corresponding to the formula ROOC—$CH_2CH_2$—[(ROOC)CHCH$_2$]$_m$—C(COOR)$_2$—[$CH_2$CH(COOR)]$_n$$CH_2CH_2$—COOR in which the R's represent alkyl groups of 1–10 carbons, and each of m and n represents zero or a positive integer such that the sum of m and n in a molecule is 0–10.

* * * * *